United States Patent [19]

Carroll et al.

[11] Patent Number: 5,036,201
[45] Date of Patent: Jul. 30, 1991

[54] PROBE AND COLLIMATOR FOR QUICK RELEASABLE MOUNTING THEREON

[75] Inventors: Robert G. Carroll, Largo, Fla.; Robin A. Wise, Jr., Morgan Hill, Calif.

[73] Assignee: Care Wise Medical Products Corporation, Morgan Hill, Calif.

[21] Appl. No.: 491,390

[22] Filed: Mar. 9, 1990

[51] Int. Cl.⁵ .............................................. G01T 1/161
[52] U.S. Cl. .............................. 250/363.10; 250/336.1; 250/505.1; 128/659
[58] Field of Search ........... 250/363.10, 336.1, 363.02, 250/368, 505.1; 128/654, 659

[56] References Cited

U.S. PATENT DOCUMENTS

| | | |
|---|---|---|
| 4,782,840 | 11/1988 | Martin Jr., et al. ................ 128/659 |
| 4,893,013 | 1/1990 | Denen et al. ..................... 250/336.1 |
| 4,959,547 | 9/1990 | Carroll et al. ................... 250/363.10 |

*Primary Examiner*—Carolyn E. Fields
*Attorney, Agent, or Firm*—Caesar, Rivise, Bernstein, Cohen & Pokotilow, Ltd.

[57] ABSTRACT

A probe and collimator to be releasably secured thereto for use in detecting, localizing, and mapping or imaging radiation emanating from a hidden source, such as within the body of a living being. The probe comprises a small body arranged to be readily held in one's hand and a radiation detector located within the body. The probe's body includes a window located at its distal end over the detector. The collimator comprises a cylindrical member adapted to be snap-fit onto the distal end of the probe body to reduce the solid angle of acceptance of radiation entering the window to a predetermined value less than that if the collimator was not in place on the probe. The collimator includes a central bore having an air vent and at least one recess extending about the inner periphery thereof and in which is located a resilient locking member, e.g., an O-ring. The body at the distal end of the probe includes at least one recess extending about the outer periphery thereof and into which the locking member is snap-fit to releasably secure the collimator to the probe. The air vent enables air to vent from the interior of the collimator to facilitate the mounting of it to the probe.

29 Claims, 2 Drawing Sheets

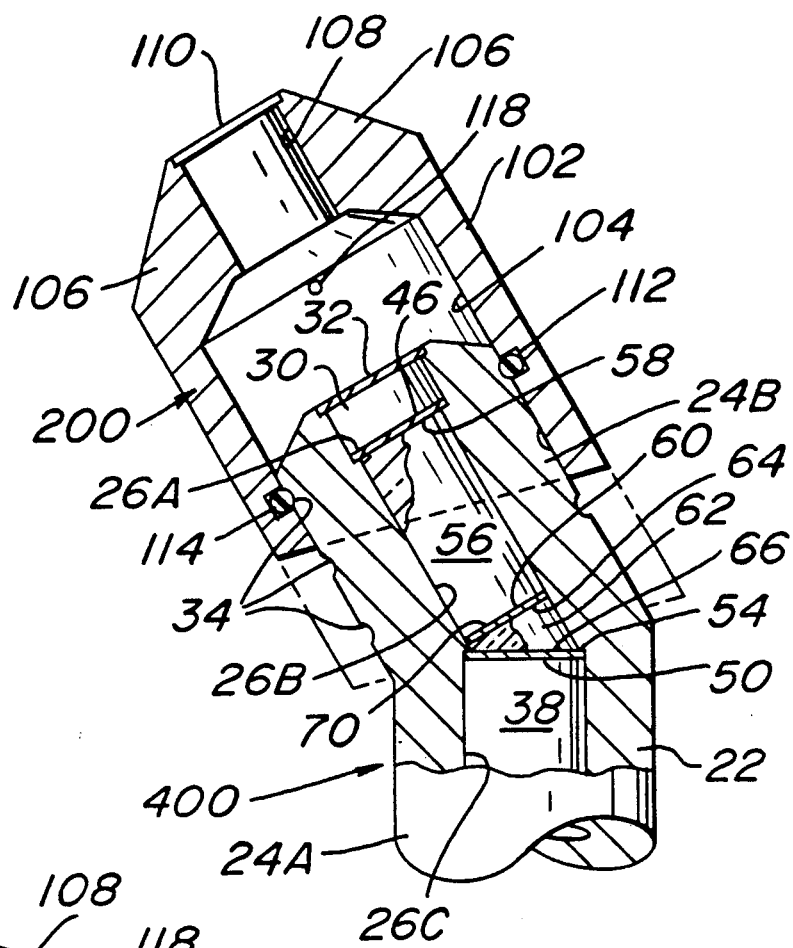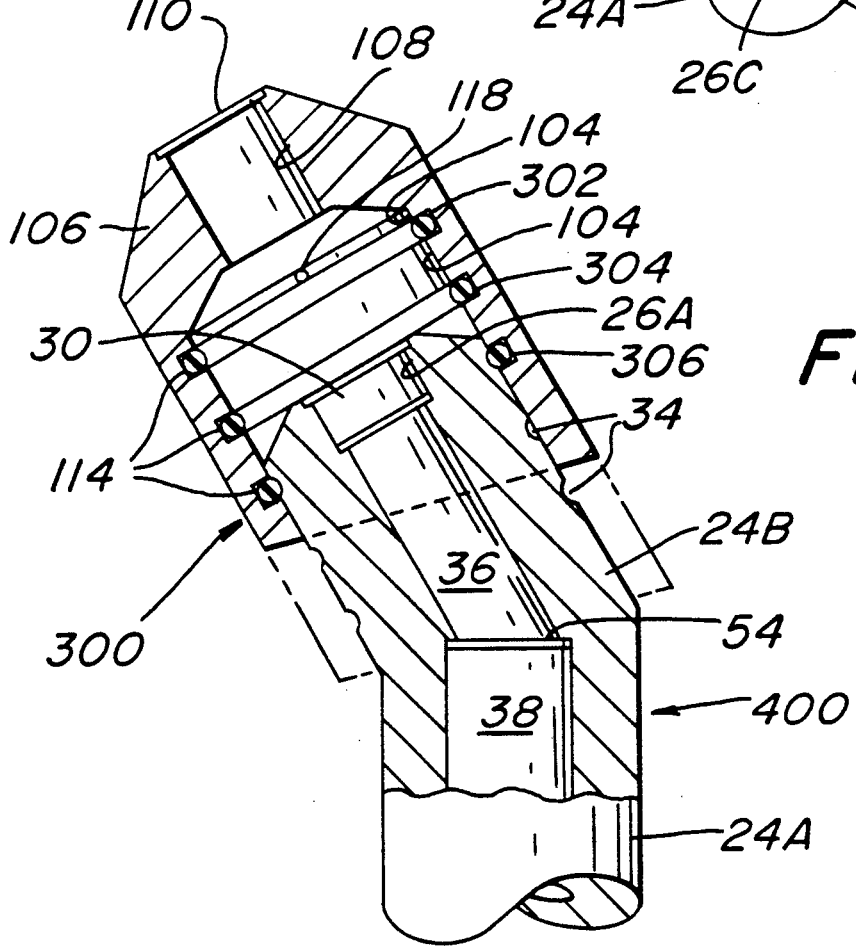

PROBE AND COLLIMATOR FOR QUICK RELEASABLE MOUNTING THEREON

BACKGROUND OF THE INVENTION

This invention relates generally to probes for detecting radiation, and more particularly to collimating probes for detecting, localizing, and imaging or mapping of radiation in biological systems or other systems.

The use of radioactive materials to tag tissue within a patient for effecting its localization and demarcation by radiation detecting services has been disclosed in the medical literature for at least forty years. Significant developments in the localization and demarcation of tissue bearing radioactive isotope tags for diagnostic and/or therapeutic purposes have occurred since that time. Thus, it is now becoming an established modality in the diagnosis and/or treatment of certain diseases, e.g., cancer, to introduce monoclonal antibodies tagged with a radioactive isotope (e.g., Iodine 125) into the body of the patient. Such monoclonal antibodies tend to seek out particular tissue, such as the cancerous tissue, so that the gamma radiation emitted by the isotope can be detected by some apparatus, e.g., a MRI or CAT scanner, to provide information and/or an image of the radiation emitting tissue.

As is known MRI and CAT scanning apparatus are extremely large, and thus not suitable for use in an operating room. Thus, while the surgeon may be able to utilize some hard copy image or data regarding the radioactively tagged tissue provided by an MRI or CAT scanner during the surgical procedure the surgeon will, nevertheless, want to manually explore various possible sites that may contain cancerous tissue to ensure that no such tissue has been overlooked or missed. Such action is typically accomplished visually and/or by palpation. Obviously, such inspection procedures are complicated by the limited amount of time available to the surgeon during the surgery, the type of cancer involved, and its possible location(s).

One type of apparatus which is small enough to be used in the operating room to assist the surgeon in detecting and localizing the presence of radioactively tagged tissue within the body of the patient makes use of a hand held radiation detecting probe. Such a probe is disposed or held adjacent portion of the patient's body where the cancerous tissue is suspected to be in order to detect if any radiation is emanating from that site, thereby indicating that cancerous tissue is likely to be found there. Unfortunately, radiation from the tagged tissue scatters off of the various surrounding body tissues organs, thereby rendering the localization of the source of the radiation difficult. Much of the indium 111 monoclonal antibody accumulates non-specifically in the liver.

One technique for localizing the radiation source is to look for the highest energy rays emanated by the radioactive isotope. This technique is based on the theory that the lower energy rays received by the probe must have undergone some scattering, whereas the higher energy rays remaining could not have undergone such scattering and must be coming from a source directly in front of the probe. While that technique has some merit it does not work well for all types of isotopes.

An alternative approach to localize the source of radiation is to utilize some device with the probe so that the surgeon or operator of the device can adjust the solid angle (cone) in which radiation can be received or accepted by the probe's detector. One such probe and associated device is commercially available from Neoprobe Corporation under the designation Neoprobe 1000. That probe makes use of three collimators, each of which can be attached in either an extended or retracted position on the probe to establish a minimum and maximum solid angle from which radiation can be detected. In particular, each of the Neoprobe 1000's collimators is a device having a different size small diameter opening which is arranged when secured to the probe in the extended position (so that its narrow diameter provides a constrained or narrowed field, i.e., the minimum solid angle of acceptance) to localize the radiation source within a small area. When the collimator is retracted or removed the solid angle of acceptance is maximum, and thus the area from which the radioactivity can be detected is significantly larger. Thus, it is suggested that when using the Neoprobe 1000 that the collimator be removed or retracted for wide angle scanning (e.g., broad survey use), and that the collimator be connected and extended for localized scanning.

In our copending U.S. Pat. Application Ser. No. 07/363,243, filed on June 8, 1989, U.S. Pat. No. 4,959,547 entitled Apparatus and Methods for Detecting, Localizing and Imaging of Radiation in Biological Systems, whose disclosure is incorporated by reference herein, and which is assigned to the same assignee as this invention, there is disclosed a collimating probe which overcomes many of the disadvantages of prior art collimating probes. In particular that probe comprises a radiation detector and an adjustment mechanism for adjusting the solid angle through which radiation may pass to the detector. That solid angle is continuously variable. The probe is constructed so that the only radiation reaching the detector is that which is within said solid angle. By adjusting the solid angle from a maximum to a minimum while moving the probe adjacent the source of radiation and sensing the detected radiation one is able to precisely locate the probe at the source of radiation. The probe can be used for diagnostic or therapeutic purposes. A receptacle is also provided to hold a specimen on the probe to detect the presence of radiation emanating therefrom.

In U.S. Pat. No. 4,801,803 (Denen et al) assigned to Neoprobe Corporation there is disclosed a probe having a distal end arranged to have a separate collimator mounted thereon to provide the probe with a higher directional aspect. The collimator for achieving that end is not shown nor described. Means are, however, shown and described for mounting the collimator to the probe. Such means comprises a first retainer groove 42 extending about the periphery of the probe's distal end, and a second retainer groove 102 disposed closely adjacent the groove 42 and formed by the edge of a shell 66 and a wall portion of the distal end of the probe when the shell 66 is disposed thereon.

The following U.S. patents relate to collimators and/or apparatus for use with x-ray or other radiation detecting equipment, e.g., x-ray machines, etc: 3,112,402 (Okun et al.), 3,310,675 (Prickett et al.), 3,628,021 (MacDonald), 3,609,370 (Peyser), 3,869,615 (Hoover et al.), 3,919,519 (Stevens), 3,936,646 (Jonker), 4,340,818 (Barnes), 4,419,585 (Strauss et al.), 4,489,426 (Grass), and 4,502,147 (Michaels).

In some applications, like the aforementioned Neoprobe prior art devices, it may be desirable or expedient to utilize a separate collimator for securement to the probe to reduce the probe's normal solid angle of acceptance. In such a case a need exists for a probe and associated collimator which are constructed so that the collimator can be readily releasably secured to the probe by means which are simple, reliable, and efficient. Moreover, probes constructed in accordance with the teachings of our aforementioned patent applications may also make use of a separate releasably securable collimator constructed in accordance with the teaching of this invention. Further still collimators may be constructed in accordance with this invention which can be releasably mounted on a probe in one of several selected positions to adjust the solid angle of acceptance to predetermined values.

OBJECTS OF THE INVENTION

It is a general object of this invention to provide a probe and a collimator therefor which overcomes the disadvantages of the prior art.

It is a further object of this invention to provide a probe and an associated collimator which may be readily secured thereto to establish at least one predetermined, lesser solid angle of acceptance of radiation from a source being examined than if no such collimator were utilized.

It is still a further object of this invention to provide a collimator may be readily secured to a conventional radiation detecting probe to establish at least one predetermined, lesser solid angle of acceptance of radiation from a source being examined than if no such collimator were utilized.

It is yet a further object of this invention to provide a collimator which includes simple, yet efficient and reliable means for enabling it to be readily secured to a radiation detecting probe to establish at least one predetermined, lesser solid angle of acceptance of radiation from a source being examined than if no such collimator were utilized.

SUMMARY OF THE INVENTION

These and other objects of this invention are achieved by providing a probe and associated collimator for detecting, localizing, mapping or imaging radiation emanating from a hidden source, e.g., within the body of a living being.

The probe comprises a body formed of a radiation blocking material, radiation detecting means located within the probe body, and first radiation transparent, closed window located at the distal end of the probe body and confronting the detecting means through which radiation may pass in a first solid angle of acceptance.

The collimator is arranged when releasably mounted on the probe to decrease the first solid angle of acceptance of radiation through the window to the detecting means. The collimator comprises a cylindrical member formed of a radiation blocking material having a cylindrical bore extending therethrough and into which the distal end of the probe body is arranged to be inserted. The bore includes an air vent communicating with the ambient atmosphere, at least one holding means (e.g., an annular recess extending about the inner periphery of the bore), and a resilient locking member (e.g., O-ring) located at the holding means. The bore also has a distal end at which a second radiation transparent, closed window is located.

The probe includes a recess extending about its outer periphery closely adjacent the distal end of the body for receipt of the resilient locking member to releasably secure the collimator to the probe when the distal end of the probe body is inserted into the bore in the collimator. The air vent enables air trapped between the distal end of the probe body and the collimator to vent to the ambient atmosphere.

DESCRIPTION OF THE DRAWINGS

Other objects and many attendant features of this invention will become readily appreciated as the same becomes better understood by reference to the following detailed description when considered in connection with the accompanying drawings wherein:

FIG. 3 is a partial sectional view of another embodiment of a probe and collimator constructed in accordance with the teachings of this invention; and FIG. 4 is a view similar to that of FIG. 3 but showing yet another embodiment of a probe and collimator constructed in accordance with this invention.

DETAILED DESCRIPTION OF THE PREFERRED EMBODIMENTS

Figure 1:
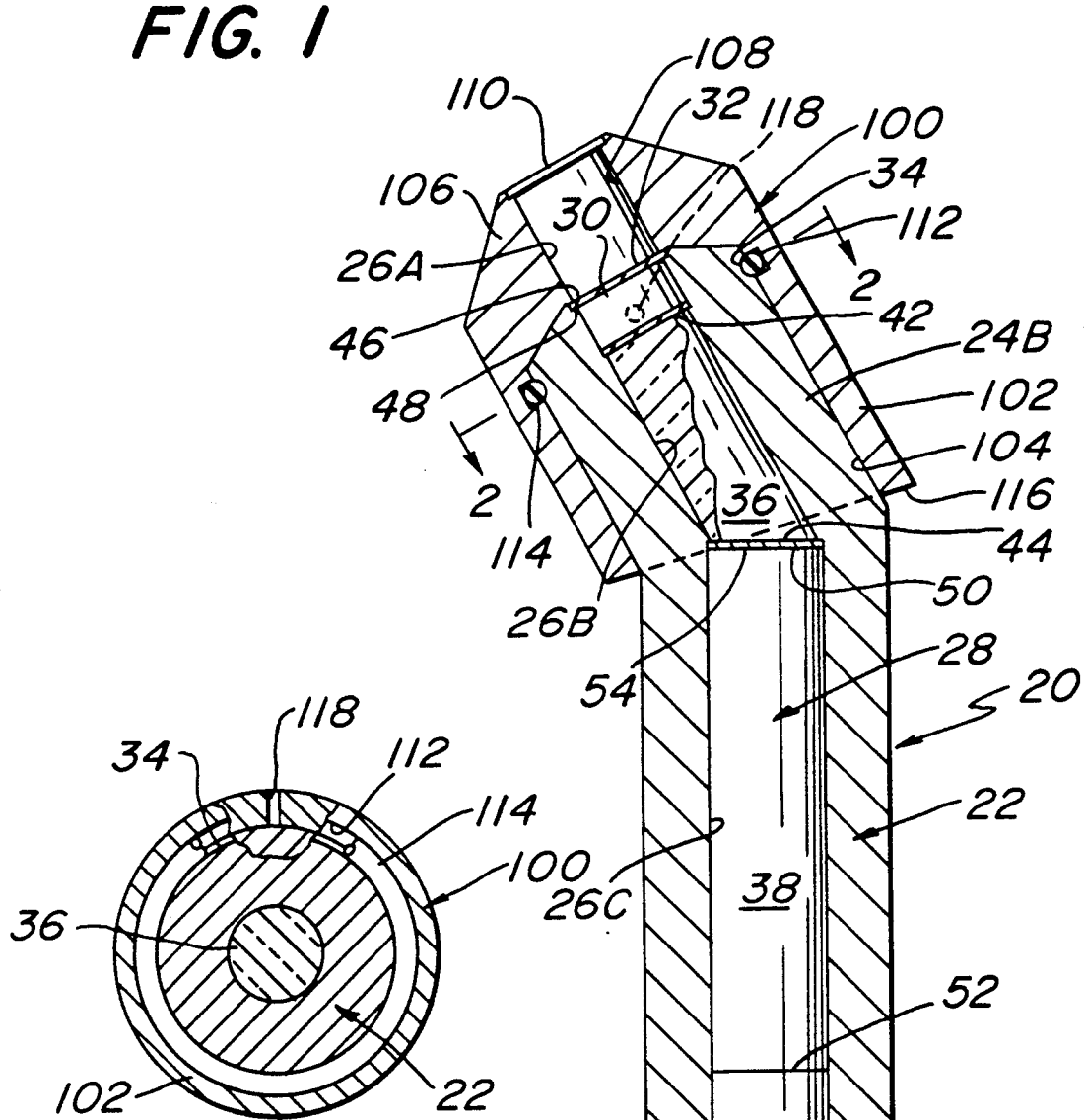
FIG. 1 is sectional view of a radiation detecting probe and associated collimator constructed in accordance with the teachings of this invention.

Referring now to various figures of the drawing wherein like reference numerals refer to like parts there is shown at 20 in FIG. 1 one embodiment of a probe and one embodiment of a collimator constructed in accordance with this invention. That probe is arranged to detect the presence of radiation emanating from a hidden source (not shown), such as tissue tagged with a radioactive isotope, and to provide electrical output signals indicative thereof via a cable or wiring harness to a conventional analyzer (not shown) or other conventional monitoring or imaging apparatus (not shown).

The collimating probe 20 includes radiation detecting means (to be described later) and is arranged to be used by itself or with a collimator constructed in accordance with this invention. One such collimator is designated by the reference numeral 100 and is shown in FIG. 1 mounted on probe 20. Two other types of collimators constructed in accordance with this invention are designated by the reference numerals 200 and 300 and are shown in FIGS. 3 and 4, respectively.

Any of the collimators 100, 200 or 300, when secured to the probe 20, as will be described in detail later, serve to reduce the normal field of view of the probe, i.e., the solid angle of acceptance of the probe's radiation detector, to some lesser angle. Depending upon the construction of the collimator it may be used to reduce the normal field of view of the probe to only a single predetermined angle (as in the case of FIG. 1) or may reduce it to one of several predetermined angles (as in the case of FIGS. 3 and 4).

The probe 20 of this invention, with any associated collimator constructed in accordance with this invention, provides significant shielding for radiation from all directions other than that within the solid angle of acceptance by virtue of the materials used and the shape and organization of the probe and the collimator. Thus, the probe 20 with or without any of the collimators 100, 200, or 300 can be used with high energy radioisotopes, such as Indium 111.

As will be appreciated by those skilled in the art Indium 111 has approximately ten times the energy of Iodine 125 (e.g., 247 KEV versus 25-30 kev). Without good shielding and collimation the use of such high energy materials would be precluded for use in some applications, e.g., detecting tagged cancerous tissue located near the liver, kidneys, or blood vessels, any of which locations would include significant accumulations of the isotope on a non-specific basis. Thus, the probes of the subject invention, by facilitating precise, preselected collimation, enable the localization of tissue, e.g., a lymph node, containing a very small amount of radiation, e.g., a few microcuries, lying adjacent to an organ containing several orders of magnitude more radiation.

The probe 20 shown in FIG. 1 basically comprises a probe body 22 having a proximal portion 24A of a generally cylindrical shape and size to be readily held in one's hand. The body portion 24A terminates in a distal portion or tip 24B extending at an acute angle, e.g., 60 degrees, to the longitudinal axis of the body portion 24A. The angular orientation of the tip 24B with respect to the hand grip portion 24A of the probe's body 22 facilitates operator comfort and ease of aiming.

The probe body 22 and the collimators 100, 200 and 300 are all formed of any suitable radiation blocking material, such as a tungsten alloy sold under the designation MIL-T-210140D by Teledyne Powder Alloys of Clifton, N.J. 07012.

The probe body 22 includes a central passageway or internal bore 26 extending therethrough in which the various components (to be described later) which make up the radiation, optical and electrical components of the probe. The bore 26 is made up of four, longitudinally disposed sections, namely, 26A, 26B, 26C, and 26D, each of which is of a respective, different inside diameter. For example, the first section 26A is of 0.416 inch (10.6 mm) inside diameter. The second section 26B is of 0.375 inch (9.52 mm) inside diameter. The third section 26C is of 0.470 inch (11.9 mm) inside diameter. The fourth section 26D is of 0.750 inch (19 mm) inside diameter.

The free end of the probe's tip 24B contiguous with the bore section 26A defines a window 30 through which radiation is received by the probe's detecting means 28 when the probe is aimed at the suspected source of radiation. The details of the radiation detecting means 28 will be described in detail later. Suffice it for now to state that such means comprises a scintillation crystal and associated components. The crystal is located within the second bore section 26B so that it confronts the window 30, whereupon the radiation blocking material of the probe's body contiguous with the window blocks the ingress of radiation so that the only radiation that reaches the crystal is that radiation within the probe's normal solid angle of acceptance (field of view). However, as noted earlier, when any of the collimators 100, 200 or 300 is mounted on the probe tip 24B the normal solid angle of acceptance of the probe itself is reduced by portions of the collimator, as will be described later.

In the interests of preventing moisture or debris from gaining ingress into the probe's bore and the crystal of the detecting means 28 located therein the window 30 includes a very thin (0.025 mm) cover sheet 32 of a radiation transmissive material, e.g., stainless steel. The cover sheet is adhesively secured, e.g., by epoxy, on a ledge at the free end of bore section 26A.

Referring now back to FIG. 1 the details of the probe's radiation detecting means 28 will now be described. To that end The detecting means 28 can take various forms. One preferred embodiment comprises a scintillation crystal 36, a photomultiplier tube 38, and voltage divider 40. The crystal 36 may be of any suitable material, e.g., sodium iodide, mercuric iodide, bismuth germanate, etc. In the embodiment shown in FIG. 1 the crystal is a cylindrical body having a planar distal end face 42 disposed perpendicularly to the longitudinal axis of the crystal, and a planar proximal end face 44 disposed at an acute angle to the longitudinal axis. The outside diameter of the crystal is just slightly less than the inside diameter of the bore portion 26B in the probe's tip, so that it can readily fit therein. A thin sealing disk 46 is disposed on the ledge 48 formed by the interface of bore sections 26A and 26B and is adhesively secured, such as by means of epoxy, thereon. The disk 46 provides an additional barrier against the ingress of moisture, thereby protecting the hygroscopic crystal 36, while also serving as a retaining member for the crystal. The disk 46 is preferably formed of stainless steel or a suitable plastic.

The photomultiplier tube 38 may be of any suitable type and basically comprises a cylindrical member, whose outside diameter is just slightly less than the inside diameter of the bore portion 26C, and has a an opposed pair of planar end faces 50 and 52, each of which is disposed perpendicularly to the longitudinal axis of the photomultiplier. The photomultiplier tube 38 is mounted within the bore portion 26C contiguous with the interface to the bore portion 26B, so that its distal end face 50 is located at that interface.

The angle of the end face 44 of the crystal 36 is the same as the angle of bore section 26B of the tip 24B to the probe body portion bore 26C, e.g., 60 degrees, so that when the crystal is in position within the bore it's angled end face 44 is located at the interface of the tip 24B and hand grip portion 24A of the probe's body, and with that end face being perpendicular to the longitudinal axis of portion 24A. Accordingly, the end face 44 of the crystal is parallel to and closely adjacent the end face 50 of the photomultiplier tube 38.

A very thin disk 54 is disposed on the ledge formed by the interface of bore sections 26B and 26C. This disk serves to retain the crystal 36 in place and prevents the ingress of moisture to the crystal from the proximal end of the probe. The disk 54 is formed of an optically transparent and index matched material, e.g., plastic, so that it can convey the light which is produced by the crystal 3 when it detects radiation to the photomultiplier tube 38. To achieve that end the disk 66 also abuts the distal end of the photomultiplier tube located in bore section 26C. If desired, the disk 54 may be formed of an optically index matched, mechanically shock absorbing material, such as an optical silicone elastomer.

In order to expedite the transmission of light between the components, the disk 54 may also be secured in place by a suitable index-matched grease or adhesive (not shown) so that it forms a good light transmissive joint with the crystal and with the end face 50 of the photomultiplier tube 38.

In FIG. 3 there is shown an alternative probe 400. The probe 400 is in most respects similar to probe 20 except for its radiation detecting means and its means for mounting a collimator onto its tip. Thus, the same reference numerals will be used to identify common features of probes 20 and 400.

As can be seen in FIG. 3, probe 400 uses an alternative detecting means to that shown in FIG. 1. In particular the alternate detecting means shown in FIG. 3 is similar in most respects to that of FIG. 1 except that does not require the crystal to have an angled proximal end for engagement with the proximal end of the photomultiplier tube 38. Thus, in the embodiment of FIG. 3 the crystal is designated by the reference numeral 56 and may be of conventional construction, i.e., include a pair of opposed planar end faces 58 and 60, each of which is perpendicular to the longitudinal axis of the crystal's body. One particularly useful crystal is that sold by Englehard Corporation of Solon, Ohio under the trademark HARSHAW POLYSCINT.

The crystal 56 is mounted within the bore section 26B of the tip 24B in the same manner as described heretofore. Since the proximal end face 60 of the crystal 56 is planar and perpendicular to the longitudinal axis of the crystal (and hence to the longitudinal axis of the bore section 26B in the tip 24B) it is not disposed parallel to the distal end face 50 of the photomultiplier tube 38 (which is located in bore section 26C). Thus, in order to convey the light from the crystal 56 to the photomultiplier tube 38 a light transmissive member or light pipe 62 is interposed between the proximal end face 60 of the crystal 56 and the sealing disk 54 located on the ledge formed at the interface of bore sections 26B and 26C.

The light pipe 60 basically comprises a cylindrical member, formed of a good light transmissive material, e.g., plastic or glass, and includes a distal end face 64 and proximal end face 66. The distal end face 64 is planar and is oriented perpendicularly to the longitudinal axis of the light pipe. The proximal end face 66 is also planar, but is disposed at the same acute angle, e.g., 60 degrees, as the bore section 26B is to the bore section 26C. Accordingly, when the light pipe 62 is in position its proximal end face 66 abuts sealing disk 54 in a good light transmissive joint. The distal end face 50 of the photomultiplier tube is also in a good light transmissive joint with the disk 54 as described heretofore. Moreover, the distal end face 64 of the light pipe abuts the proximal end face 60 of the crystal 56 in a good light transmissive joint, via another very thin, optically transparent, index-matched sealing disk 70. The disk 70, like disk 54, may be formed of a mechanical shock absorbing optically index matched material. In order to expedite the light transmission between all of the foregoing joints an index-matched grease or adhesive (not shown) may be provided at the abutting faces.

In either embodiment of FIGS. 1 or 3 the voltage divider 40 circuit is located within the bore section 26C distally of the photomultiplier tube's proximal end face 52. The voltage divider circuit itself is disposed within a cylindrical housing whose outside diameter is just slightly less than the inside diameter of the bore section 26C and is held in place by a biasing spring (not shown). An electrical cable 72 (FIG. 1) extends from the voltage divider through bore section 26D. As can be seen in FIG. 1 the proximal end of the bore section 26D include an internally threaded throat 74 which is adapted to receive a mating end cap (not shown). The cable 72 extends through a opening in the end cap for connection to suitable monitoring apparatus (not shown).

As can be seen clearly in FIG. 1 a groove or recess 34 extends about the periphery of the tip 24B immediately adjacent the free end thereof at which the window 30 is located. This groove forms one portion of the means for enabling the releasable securement of the collimator 100 to the probe tip 24B. The other components making up the releasable securement means form a portion of the collimator itself and will be described later.

Figure 2:
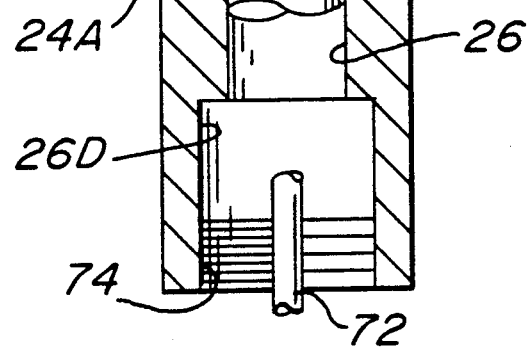
FIG. 2 is a sectional view taken along line 2—2 of FIG. 1.

As can be seen in FIGS. 1 and 2 the collimator 100 basically comprises a cylindrical shell having a sidewall section 102 defining an internal bore 104. The internal diameter of the bore is just slightly larger than the external diameter of the probe tip 24B to enable the probe tip to be closely received therein. The distal end of the collimator includes a conical wall section 106 having a central bore 108 therein. The bore 108 forms the window of the collimator. Like probe 20 the window 108 of the collimator 100 includes a very thin (0.025 mm) cover sheet 110 of any suitable radiation transmissive material, e.g., stainless steel, thereover.

An annular recess or groove 112 is located within the bore 104 of the collimator 100 and located closely adjacent the interface of the conical wall section 106 with cylindrical wall section 102. This recess 112 is arranged to receive and retain a resilient locking member 114 therein. The resilient member 114 preferably comprises an 0-ring and serves as another component of the means for releasably securing the collimator 100 to the probe 20. The ring may be formed of any suitable material, such as neoprene rubber, nylon, steel or some other suitable metal (in the case where the material making up the ring is not resilient, e.g., is a metal, the ring is preferably split so that it can be readily inserted within the recess 112). In order to ensure that the ring 114 is trapped within the recess 112, that recess is of a greater depth than the groove 34 in the probe tip 24B. Moreover, the recess 112 includes square corners to ensure that the ring is retained permanently within it.

The collimator 100 is mounted on the probe tip 24B in the following manner. The probe tip 24B is inserted into the open end 116 of the bore 104 of the collimator and slid through the bore fully into the collimator, at which time the collimator's locking ring 114 reaches the probe's recess 34. Owing to the resiliency of the ring 114 and the shallow rounded corner nature of the recess 34 the ring 114 snap-fits into the recess easily, thereby releasably securing the collimator to the probe tip at that longitudinal position. Removal of the collimator 100 can be readily effected by merely pulling the collimator away from the probe tip, whereupon the ring 114 moves out of the recess 34 in the probe tip (the deep square cornered recess 112 serving to ensure that the ring 114 remains in that recess).

As can be seen clearly in FIG. 2 the collimator includes venting means 118 in communication with the interior of the collimator 100 and also with the ambient atmosphere, so that when the collimator 100 is secured to the probe tip 24B any air that would be trapped within the collimator between the interior surface of its bore 104, the exterior surface of the probe tip 24B and the 0-ring 114 will quickly vent to the ambient atmosphere. This feature ensures that air within the collimator 100 will not interfere with the rapid and reliable mounting of the collimator onto the probe tip. Moveover, the fact that the ring 114 is located at the interface of collimator wall sections 102 and 106, and hence very close to the free end of the probe tip when the collimator is in place, ensures that the air space within the collimator is kept to an absolute minimum, thereby further ensuring that any air within the collimator will not impede the mounting of the collimator onto the probe.

The venting means 118 may take any suitable form. In the preferred embodiment of this invention such means comprises a vent hole 118 extending radially out through the sidewall 102 and in communication with the internal bore 104 and the ambient atmosphere.

It must be pointed out at this juncture that the collimator 100 may take many forms and configurations. Thus, other collimators 100 having different dimensions, wall thicknesses, etc. may be constructed for use with probe 20, so that each collimator establishes a different solid angle of acceptance of radiation. Accordingly, the person using the probe 20 can establish the desired field of view by the selection and mounting of the appropriately configured collimator 100 onto the probe 20.

As should be appreciated by those skilled in the art other types of resilient locking means may be used in lieu of the heretofore described ring 114. Thus, spring loaded ball bearing pressure retainers (not shown) could be inset within the collimator wall 102 (with such an embodiment the need for the ring holding recess 112 is obviated). So too, a ring (not shown) composed of various configurations of spring metal protuberances may be incorporated into the collimator to mate with the groove 34 in the probe's tip.

Operation of the probe 20 is a follows: The probe is first used without any collimator so that the maximum field of view is established (i.e., the maximum field of view being the normal solid angle of acceptance as established by the probe's geometry). Thus the tip 24B of the probe 20 is brought adjacent the portion of the patient's body to be examined so that the general location of the emanated radiation can be readily found (without any collimator thereon the probe will be at its maximum sensitivity). The probe's solid angle of acceptance of the probe may then be reduced to a particular intermediate setting by the selection and mounting of an appropriately configured collimator 100 on the probe tip 24B. The user then monitors the radiation detected and moves the probe with the collimator thereon in response to that detected radiation to center the probe over the source. If successively narrow field establishing collimators 100 are desired the foregoing sequence of operation continues until the probe is at its narrowest solid angle of acceptance (i.e., has the narrowest field establishing collimator 100 thereon) and still receiving radiation. At this point the user can be sure that the source of that radiation is directly opposite the collimator's window.

In FIG. 3 the probe 400 is shown. As can be the probe tip 24B of probe 400 is modified to include a plurality of spaced apart peripheral recesses 34. This arrangement enables a collimator 200 to be mounted on the probe at any of those recesses, thereby enabling the collimator 200 to establish different, respective fields of view for the probe 400. As can be seen in FIG. 3 the collimator 200 is similar to that of collimator 100 shown in FIG. 1 except that the recess 112 and ring 114 located therein is located further proximally. Thus, with such an arrangement all that is necessary to change the field of view of the probe is to move the collimator to the desired longitudinal position on the probe tip between the solid and phantom line positions shown in FIG. 3.

In FIG. 4 there is shown the collimator 300 mounted on probe 400. This collimator is also arranged to provide different respective fields of view for the probe. The collimator 300 is similar in most respects to the collimator 200 except for the releasable securement means utilized. Thus, in the interest of brevity the structural features which are common to both collimators 200 and 300 will be given the same reference numerals and those features will not be described at length hereinafter.

The means for releasably mounting the collimator 300 onto the probe tip 24B of probe 400 basically comprises holding means in the form of a plurality of recesses 302, 304, and 306 which extend about the periphery of the bore 104 of collimator 300. Each recess 302-306 is constructed similarly to the sharp cornered recess 112 of the collimators 100 and 200 in order to permanently receive and retain a respective one of plural locking rings 114 therein.

The collimator 300 is mounted on the probe's tip 24B by inserting that tip within the collimator's bore 104 so that the ring 114 in a desired one of the grooves 300-306 is located opposite to one of the recesses 34 in the probe's tip at the desired longitudinal position for the collimator. Accordingly, the ring 114 will snap-fit into that recess 34, in a similar manner as described heretofore, thereby holding the collimator 300 in place at that particular longitudinal position along the tip. This action establishes a particular reduced field of view for the probe. It must be pointed out at this juncture that only one recess 34 need be provided in the probe's tip 24B to accommodate any of the rings 114. In fact, such an arrangement may be preferable since the elimination of each recess 34 means there is more shielding material, e.g., tungsten alloy, to provide additional shielding for the crystal from radiation through the sidewall of the tip portion 24B.

Like collimator 200, collimator 300 when mounted on probe tip 24B of a probe 400 can establish three respective fields of view for the probe. Thus, recess 302 establishes the largest of the reduced fields of view of the probe 400 when the collimator 300 is mounted thereon, while the recess 304 establishes an intermediate field of view, and recess 306 establishes the narrowest field of view.

The recesses 302-306 may be equidistantly spaced from one another or may be spaced apart by predetermined differing distances so that any discrete desired field of view between maximum (which is shown in phantom lines) an a minimum (which is shown in solid lines) may be established.

In order to change the field of view of the probe 400 from that established by the then existing setting (location) of the collimator 200 or 300 on the probe tip 24B all that is required is to pull or push the collimator along the tip to the desired longitudinal position. The releasable securement means of the probe and collimator of this invention enables such action to be accomplished readily, reliably and with accuracy and precision. In this regard when the collimator is pulled or pushed longitudinally from any set position on the probe's tip the ring 114 in the recess 34 exits that recess. Continued pulling or pushing on the collimator moves the collimator with respect to the probe's tip until a ring 114 is located opposite to desired recess 34 in probe's tip, whereupon the ring snap fits into that recess to hold the collimator in that position, and thus establishes the new field of view of the probe.

As should be appreciated from the foregoing the probes/collimators constructed in accordance with this invention provide the surgeon or other user with means for readily establishing a predetermined desired field of view of the probe to enable him/her to methodically find radiologically tagged tissue that he/she could not otherwise see or feel. That tissue can then be removed or otherwise treated.

Without further elaboration the foregoing will so fully illustrate our invention that others may, by applying current or future knowledge, adopt the same for use under various conditions of service.

We claim:

1. A probe and collimator for ready releasable mounting thereon, said probe being arranged for detecting radiation emanating from a hidden source when held adjacent said hidden source, said probe comprising a probe body formed of a radiation blocking material, radiation detecting means located within said probe body, and a first radiation transparent, closed window located at the distal end of said probe body and confronting said detecting means through which radiation may pass in a first solid angle of acceptance, said collimator being arranged when releasably mounted on said probe to decrease said first solid angle of acceptance of radiation through said first window to said detecting means, said collimator comprising a cylindrical member formed of a radiation blocking material having a cylindrical bore extending therethrough and into which said distal end of said probe body is arranged to be inserted, said bore including an air vent in communication with the ambient atmosphere, at least one holding means located at a fixed position in the inner periphery of said bore, and a resilient locking member held by said holding means thereat, said bore also having a distal end at which a second radiation transparent, closed window is located, said probe including at least one recess extending about the outer periphery thereof adjacent the distal end thereof for receipt of said locking member to releasably secure said collimator to said probe when said distal end of said probe body is inserted into said bore in said collimator, with said air vent enabling air trapped between said distal end of the probe body and said collimator to vent to the ambient atmosphere.

2. The probe and collimator of claim 1 wherein said holding means comprises an annular recess extending about the periphery of said bore of said collimator and wherein said resilient locking member comprises a ring.

3. The probe and collimator of claim 1 wherein said recess in said probe body is located closely adjacent the distal end of said probe body and wherein said resilient locking member of said collimator is located adjacent the window of said collimator to minimize the volume of air space enclosed between the outer surface of the probe, and the inner surface of the collimator's bore located distally of the locking member.

4. The probe and collimator of claim 3 wherein said holding means comprises an annular recess extending about the periphery of said bore of said collimator and wherein said resilient locking member comprises a ring.

5. The probe of and collimator of claim 1 wherein said holding means comprises an annular recess extending about the periphery of said bore and which is deeper than said recess in said probe body to ensure that said locking means remains seated within the recess in said collimator.

6. The probe and collimator of claim 5 wherein said resilient locking member comprises a ring.

7. The probe and collimator of claim 1 wherein said probe includes plural recesses extending about the outer periphery thereof and wherein said collimator comprises a plurality of spaced-apart locking members, each of said locking members being located at respective longitudinal positions in the periphery of said bore, each of said locking members being arranged to cooperate with a selected one of said recesses in said probe when said collimator is mounted on said probe to reduce said predetermined solid angle of acceptance of radiation to respective lesser value.

8. The probe and collimator of claim 7 wherein said holding means comprises a plurality of spaced apart annular recesses in the periphery of said bore of said collimator and wherein each of said resilient locking members comprises a ring.

9. The probe and collimator of claim wherein said probe body includes an elongated linear hand grip portion and a linear tip portion extending at an acute angle thereto, said probe body including a first bore extending through said tip portion and a second bore extending through said hand grip portion, said bores extending at said acute angle to each other and communicating with each other, said radiation detecting means comprising a photomultiplier tube located in said second bore and a scintillation crystal located within said first bore, said crystal and said bore being in good light communication with each other via a light transmissive interface.

10. The probe and collimator of claim 9 wherein said crystal has a longitudinal axis parallel to the longitudinal axis of said first bore, and said photomultiplier tube has a longitudinal axis parallel to the longitudinal axis of said second bore, and wherein said light transmissive interface is formed by a planar proximal end face of said crystal and a planar end face of said photomultiplier tube, said end face of said crystal extending at said acute angle to the longitudinal axis of said crystal, said end face of said photomultiplier tube extending perpendicularly to the longitudinal axis of said photomultiplier tube.

11. The probe and collimator of claim 10 additionally comprising a light transmissive material interposed between said planar end face of said crystal and said planar end face of said photomultiplier tube.

12. The probe and collimator of claim 11 wherein said material is a mechanical shock absorbing material.

13. The probe and collimator of claim 9 wherein said light transmissive interface comprises a cylindrical member formed of an optically transmissive material located within one of said first and second bores between said crystal and said photomultiplier tube, said cylindrical member having a longitudinal axis parallel to the longitudinal axis of said bore, a planar distal end face, and a planar proximal end face, said crystal having a planar proximal end face disposed perpendicularly to the longitudinal axis of said first bore and arranged to abut said distal end face of said cylindrical member in a good light tight joint, said photomultiplier tube having a planar distal end face disposed perpendicularly to the longitudinal axis of said second bore and arranged to abut said proximal end face of said cylindrical member in a good light transmissive joint.

14. The probe and collimator of claim 13 additionally comprising a light transmissive material interposed between said planar end faces making up said joints.

15. The probe and collimator of claim 14 wherein said material is a mechanical shock absorbing material.

16. The probe and collimator of claim 13 wherein said cylindrical member is located within said first bore, and wherein said distal end face of said cylindrical member extends perpendicularly to the longitudinal axis of said first bore, said proximal end face of said cylindrical member extending at said acute angle to said longitudinal axis of said first bore.

17. The probe and collimator of claim 16 additionally comprising a light transmissive material interposed between said planar end faces making up said joints.

18. The probe and collimator of claim 17 wherein said material is a mechanical shock absorbing material.

19. A collimator for ready releasable mounting on a probe, said probe being arranged for detecting radiation emanating from a hidden source when held adjacent said hidden source, said probe comprising a probe body formed of a radiation blocking material, radiation detecting means located within said probe body, and a first radiation transparent, closed window located at the distal end of said probe body and confronting said detecting means through which radiation may pass in a first solid angle of acceptance, said collimator comprising a cylindrical member formed of a radiation blocking material and means for releasably mounting it on said probe to decrease said first solid angle of acceptance of radiation through said first window to said detecting means, said mounting means comprising a cylindrical bore extending through said cylindrical member and into which said distal end of said probe body is inserted, at least one holding means at the inner periphery of said bore, and a resilient locking member held by said holding means, said bore also having a distal end at which a second radiation transparent, closed window is located, said probe including at least one recess extending about the outer periphery thereof adjacent the distal end thereof receiving said locking member therein to releasably secure said collimator to said probe when said distal end of said probe body is inserted into said bore in said collimator, said collimator including air vent means in communication with the ambient atmosphere whereupon said air vent means enables air trapped between said distal end of the probe body and said collimator to vent to the ambient atmosphere.

20. The collimator of claim 19 wherein said holding means comprises an annular recess extending about the periphery of said bore of said collimator and wherein said resilient locking member comprises a ring.

21. The collimator of claim 19 wherein said recess in said probe body is located adjacent the distal end of said probe body and wherein said holding means comprises an annular recess extending about the periphery of said bore of said collimator located adjacent said window of said collimator to minimize the volume of air space enclosed between the outer surface of the probe, and the inner surface of the collimator's bore located distally of the resilient locking member.

22. The collimator of claim 21 wherein said resilient locking member comprises a ring.

23. The collimator of claim 19 wherein said holding means comprises an annular recess extending about the periphery of said bore of said collimator, said annular recess being deeper than said recess in said probe body to ensure that said resilient locking member remains seated within the recess in said collimator.

24. The collimator of claim 23 wherein said resilient locking member comprises a ring.

25. The collimator of claim 21 wherein said recess in said collimator is deeper than said recess in said probe body to ensure that said resilient locking member remains seated within the recess in said collimator.

26. The collimator of claim 25 wherein said resilient locking member comprises a ring.

27. The collimator of claim 19 wherein said collimator comprises a plurality of spaced-apart resilient locking members, each of said resilient locking members being located at a respective longitudinal position in the periphery of said bore, each of said locking members being arranged to cooperate with said at least one recess in said probe when said collimator is mounted on said probe to reduce said predetermined solid angle of acceptance of radiation to a respective lesser value.

28. The collimator of claim 27 wherein said holding means comprises a plurality of annular recesses extending about the periphery of said bore of said collimator, said annular recess being spaced apart longitudinally, with each of said annular recesses holding a respective one of said resilient locking members.

29. The collimator of claim 28 wherein each of said resilient locking members comprises a ring.

* * * * *